(12) United States Patent
Levin

(10) Patent No.: US 9,675,497 B1
(45) Date of Patent: Jun. 13, 2017

(54) UNDERGARMENT WEARABLE PATIENT MONITOR

(71) Applicant: Paul D. Levin, Vellejo, CA (US)

(72) Inventor: Paul D. Levin, Vellejo, CA (US)

(*) Notice: Subject to any disclaimer, the term of this patent is extended or adjusted under 35 U.S.C. 154(b) by 0 days.

(21) Appl. No.: 15/278,950

(22) Filed: Sep. 28, 2016

(51) Int. Cl.
| | |
|---|---|
| *G08B 23/00* | (2006.01) |
| *A61F 13/42* | (2006.01) |
| *A61B 5/00* | (2006.01) |
| *A61F 13/49* | (2006.01) |
| *A61B 5/11* | (2006.01) |
| *A41B 9/00* | (2006.01) |

(52) U.S. Cl.
CPC .............. *A61F 13/42* (2013.01); *A41B 9/001* (2013.01); *A61B 5/1114* (2013.01); *A61B 5/447* (2013.01); *A61B 5/6804* (2013.01); *A61B 5/6808* (2013.01); *A61F 13/49* (2013.01); *A61B 2562/029* (2013.01); *A61B 2562/0219* (2013.01); *A61F 2013/424* (2013.01)

(58) Field of Classification Search
CPC .......... A61B 5/00; A61B 5/08; A61B 5/6804; A61B 5/6808; A61B 5/1114; A61B 5/447; A61F 13/42; A61F 13/49; G08B 23/00
USPC .... 340/573.1, 573.5, 506, 539.11, 604, 669; 600/300–301; 128/903–904
See application file for complete search history.

(56) References Cited

U.S. PATENT DOCUMENTS

| | | | |
|---|---|---|---|
| 4,106,001 A | 8/1978 | Mahoney | |
| 5,266,928 A | 11/1993 | Johnson | |
| 5,469,145 A | 11/1995 | Johnson | |
| 6,573,837 B2 | 6/2003 | Bluteau | |
| 6,603,403 B2 | 8/2003 | Jeutter | |
| 7,053,781 B1 | 5/2006 | Haire | |
| 7,394,391 B2 | 7/2008 | Long | |
| 7,477,156 B2 | 1/2009 | Long | |
| 8,111,165 B2 | 2/2012 | Ortega | |
| 8,299,317 B2 | 10/2012 | Tippey | |
| 8,416,088 B2 | 4/2013 | Ortega | |
| 8,772,568 B1 | 7/2014 | Ramirez | |
| 2004/0220538 A1* | 11/2004 | Panopoulos | ............ A61F 13/42 604/361 |
| 2011/0263950 A1* | 10/2011 | Larson | .................. A61B 5/1113 600/301 |
| 2012/0268278 A1 | 10/2012 | Lewis | |
| 2014/0121473 A1* | 5/2014 | Banet | .................. A61B 5/0015 600/301 |
| 2014/0266736 A1* | 9/2014 | Cretu-Petra | ............. A61F 13/42 340/573.5 |
| 2016/0310329 A1* | 10/2016 | Patel | ....................... A61F 13/42 |

* cited by examiner

*Primary Examiner* — Hung T Nguyen

(57) ABSTRACT

A patient monitor apparatus utilizing a base member having first and second surfaces used in conjunction with an undergarment. The base member first surface supports a moisture sensor which generates a signal upon the presence of urine. A tilt sensor is also mounted to the base member and generates a signal upon the absence of certain movements of the patient. The moisture sensor is covered by a porous sheet which prevents premature alarms from moist skin.

15 Claims, 6 Drawing Sheets

UNDERGARMENT WEARABLE PATIENT MONITOR

BACKGROUND OF THE INVENTION

Urinary incontinence, the loss of bladder control, is a very common condition in elderly patients. The severity of urinary incontinence ranges from occasionally leaking urine to having an uncontrollable urge to urinate before reaching a toilet in time. Of the approximately 1.7 million patients in convalescent hospitals and nursing homes in the United States at the present time, half of such patients are deemed to be incontinent.

The present routine in most nursing homes in the United States is to check all patients every two hours around the clock for urinary leakage and to change a patient to a dry undergarment when wetness is discovered. Although this method of treatment of urinary incontinence helps to maintain the dryness of undergarments of patients, patients may be unnecessarily disturbed when they are dry and, conversely, may become wet again shortly after being changed. In the latter case, the patient would remain in a wet condition for as much as two hours.

Another frequently encountered problem in nursing homes is the development of a decubitus ulcer, also known as a pressure ulcer, a pressure sore, or a bed sore. The development of decubitus ulcers is due to the infrequent turning or change of position in bed by elderly patients. Rounds commonly made every two hours by caregiver to assure timely turning of a patient may be insufficient for noting patient movement. The situation is especially prevalent in lean or cachectic subjects who are especially liable for developing decubitus ulcers. It should also be noted that decubitus ulcers develop through pressure, shearing, and moisture, the latter commonly deriving from incontinence.

In the past, many systems of detecting incontinence and other patient conditions have been proposed. For example, U.S. Pat. Nos. 4,106,001, 5,266,928, 5,469,145, 6,603,403, 7,394,391, 7,477,156, and 8,299,317 disclose employing one or more conductive elements which are in direct contact with moisture expelled by a patient to produce an electrical signal which triggers an alarm indicating the presence of urinary moisture.

U.S. Pat. No. 8,772,568 shows an incontinence detection system which employs a disposable sensor that is attached to a diaper-like assembly worn around the waist of the of the patient.

U.S. Pat. Nos. 6,573,837, 7,053,781, and United States Patent Publication 2012/0268278 describe incontinence monitoring systems that employ a metallic element sensor in combination with adhesive and layered pads that lie between the metallic sensors and the skin of the patient.

U.S. Pat. Nos. 8,111,165 and 8,416,088 show a patient sensor system that utilizes an incontinence or moisture detector in direct contact with the skin of the patient in combination with a pressure sensor to detect contact of the patient's skin with a support.

An incontinence detector having reusable elements in combination with a tilt sensor to avoid the development of decubitus ulcers would be a notable advance in the medical arts.

SUMMARY OF THE INVENTION

In accordance with the present application, a novel and useful bed patient monitor apparatus is herein provided.

The apparatus of the present application includes a base member that has a first surface and an opposite second surface. The present apparatus is intended for use with a conventional undergarment or diaper normally worn patients suffering from incontinence. The second surface of the base member is intended to lie against such undergarment.

A moisture sensor is also employed in the present invention and a portion is positioned under the first surface of the base member case. The moisture sensor is configured to generate a signal, preferably a radio signal, upon the detection of moisture by the use of metallic conductors that react to increase in conductivity between the conductors due to moisture such as urine. A porous sheet is positioned over the first surface and is intended to contact the skin of the patient and to isolate the metallic elements of the sensor from the skin of the patient. The porous sheet may take the form of a mesh fabric that has a memory and is fastened to the base member to allow rotation or separation relative to the base member. The porous sheet is of sufficient durability to be reused after cleaning and to return itself to its original position against the moisture sensor through the memory possessed by the porous sheet, which may take the form of a plastic material.

In addition, the apparatus of the present invention possesses a tilt sensor. The tilt sensor is mounted to the base and is configured to generate a signal, preferably a radio signal, indicating the absence of turning of the patient during a selected time period. In this manner, caregivers are alerted to the possibility of the development of decubitus ulcers by a patient remaining against a surface, such as a bed, for prolonged periods of time.

It may be apparent that a novel and useful patient monitor apparatus has been heretofore described.

It is therefore an object of the present application to provide a bed patient monitor apparatus that includes a device which detects wetness in an undergarment due to a patient's incontinence.

Another object of the present application is to provide a patient monitor apparatus that is relatively small and wearable, being compatible with undergarments found in the prior art.

Another object of the present application is to provide a bed patient monitor apparatus which may be used with a moisture detection sensor in combination with a tilt sensor to provide information which allows caregivers to remove a wet undergarment and substitute a dry one therefor, as well as to turn a patient to prevent the development of decubitus ulcers due to excessive pressure and/or moisture against the skin of the patient.

Another object of the present application is to provide a bed patient monitor apparatus that includes a moisture sensor isolated from the skin of the patient by a porous sheet which is separable from the moisture sensor base and returns to its position against the moisture sensor base due to the memory characteristic of the porous sheet.

Another object of the present application is to provide a bed patient monitor apparatus that is capable of obtaining a signal and transmitting said signal to a caregiver to provide information such as identity of the patient, patient's room, the bed number of the patient, and the like.

Another object of the present application is to provide a bed patient monitor apparatus that reliably generates a signal to indicate to a caregiver the amount of motion of the patient as well as the positional change of the patient during a certain period and transmitting a signal representative of the same to a display accessible to the caregiver.

Yet another object of the present application is to provide a bed patient monitor apparatus which is accurate and not subject to the generation of false signals indicating incontinence of the patient.

The application possesses other objects and advantages especially as concerns particular characteristics and features thereof which will become apparent as the specification continues.

Figure 1:
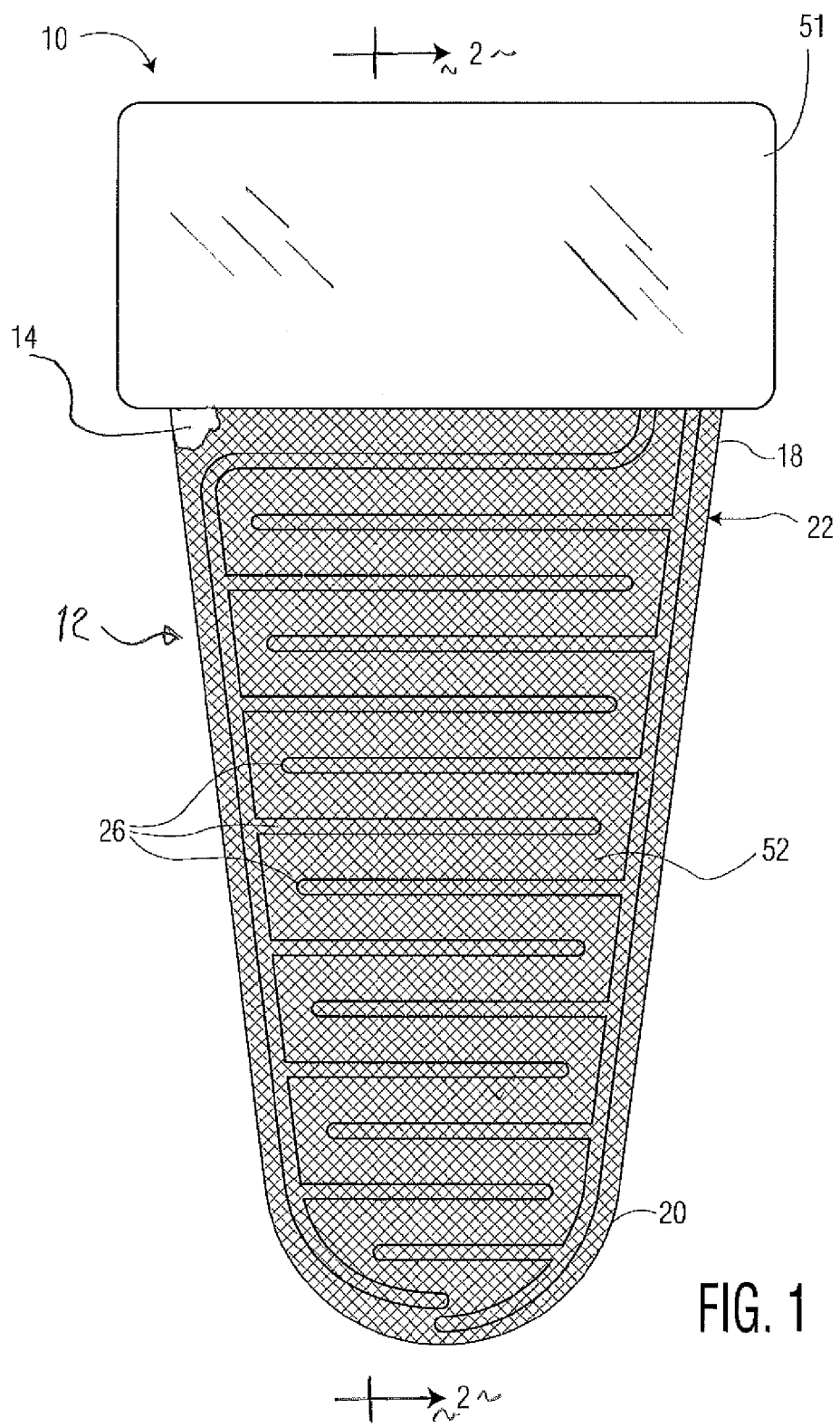
FIG. 1 is a top plan view of the apparatus of the present application in its assembled condition.

For a better understanding of the invention, reference is made to the following detailed description of the preferred embodiments thereof which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior delineated drawings.

The wearable apparatus sought for patenting as a whole is identified in the drawings by reference character 10. Apparatus 10 includes as one of its elements a base member 12, best shown in FIGS. 1 and 2. Base member 12 includes a first surface 14, which is intended to lie against a patient's skin, and an opposite second surface 16. Second surface 16 is intended to lie against an undergarment, which will be described in greater detail as the specification continues. Base member 12 may be formed of any suitable rigid or semi rigid material. As depicted in the drawings, a moisture sensor 22 on base member 12 is made from a flexible material and is tapered from a top portion 18 to a rounded bottom portion 20, FIG. 1. Typically, base member 12 is approximately 20 cm. long, 9 cm. across top portion 18, and 5 cm. across bottom portion 20. Needless to say, base member 12 of apparatus 10 is relatively compact in size.

Figure 2:
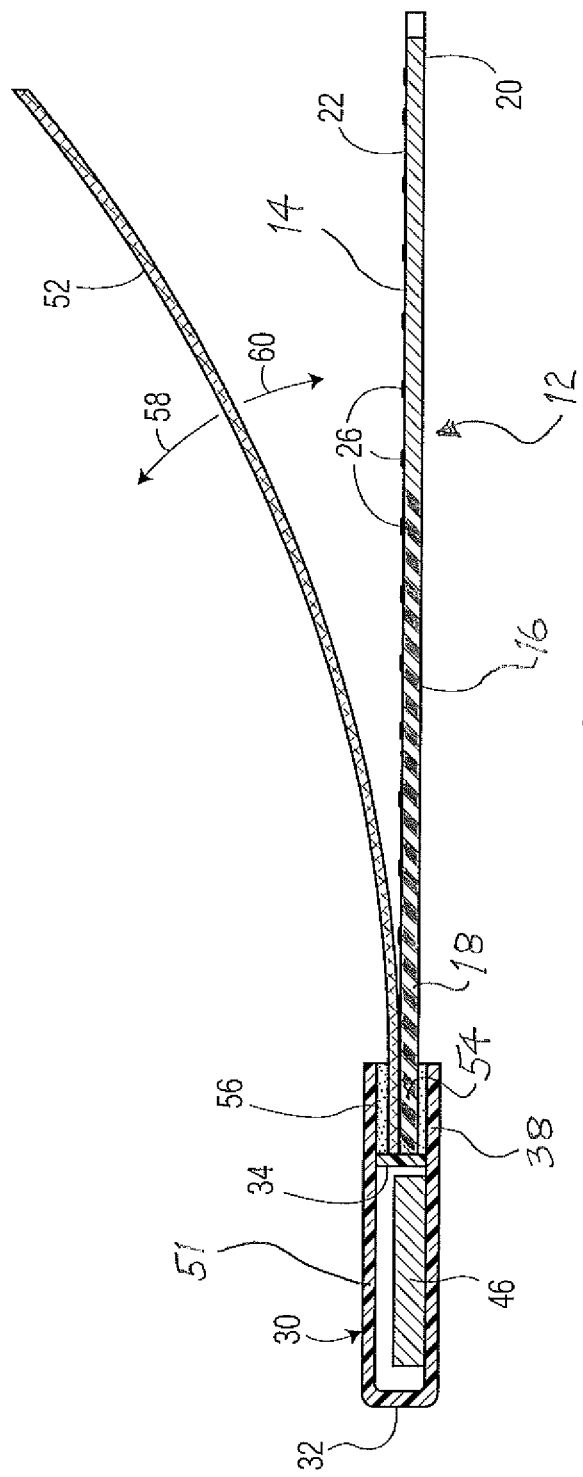
FIG. 2 is a sectional view taken along line 2-2 of FIG. 1 indicating the memory and bending characteristic of the porous mesh attached to the sensor base, such mesh being depicted with an exaggerated thickness for the sake of clarity.

Moisture sensor 22 carries a plurality of metallic traces or strips 26 disposed on top surface 14 of base member 12 in a looped, generally parallel configuration, FIGS. 1 and 2. It should be apparent that any urine disposed on sensor 22 between any of a pair of plurality of traces 26 will allow conduction of electrical current therebetween and will generate a signal sent to electronic components 28 within case 30 of base member 12, shown in FIG. 3. Again, such signal generation may be a radio signal and is of conventional configuration.

Figure 3:
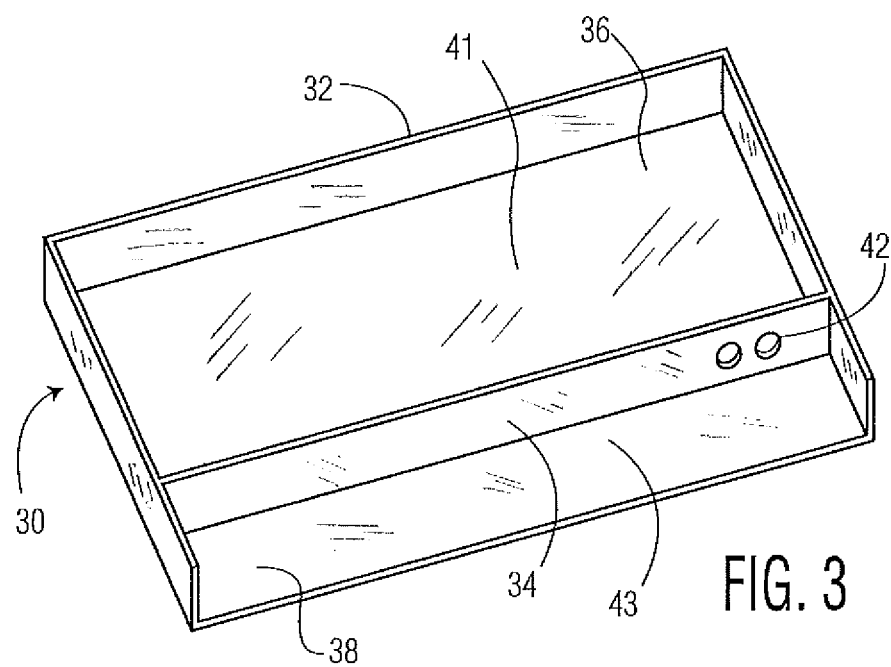
FIG. 3 is a front, left side, bottom, perspective view of the component case prior to integration into the apparatus depicted in FIG. 4.

Referring now to FIG. 3, it may be observed that a case 30 is depicted that includes a perimeter wall 32 and an interior partition 34. Bottom 36 of case 30 supports electronic components 28, depicted in FIG. 4. Base member case 30 possesses a first or upper compartment 41 and a second or lower compartment 43. A shelf 38 is formed by interior partition 34 against bottom 36. Looking again at FIG. 4, it may be seen that a pair of wires 40 attached to metal traces 26 pass through transverse holes 42 and to a circuit board 44 on bottom 36 of case 30. Among the specific components of plurality of components 28 is a battery 46 and a tilt sensor 48, the importance of which will be described hereinafter. A pair of wires 50 link battery 46 to circuit board 44. Cover 51 encloses case 30 as depicted in FIG. 1.

Figure 4:
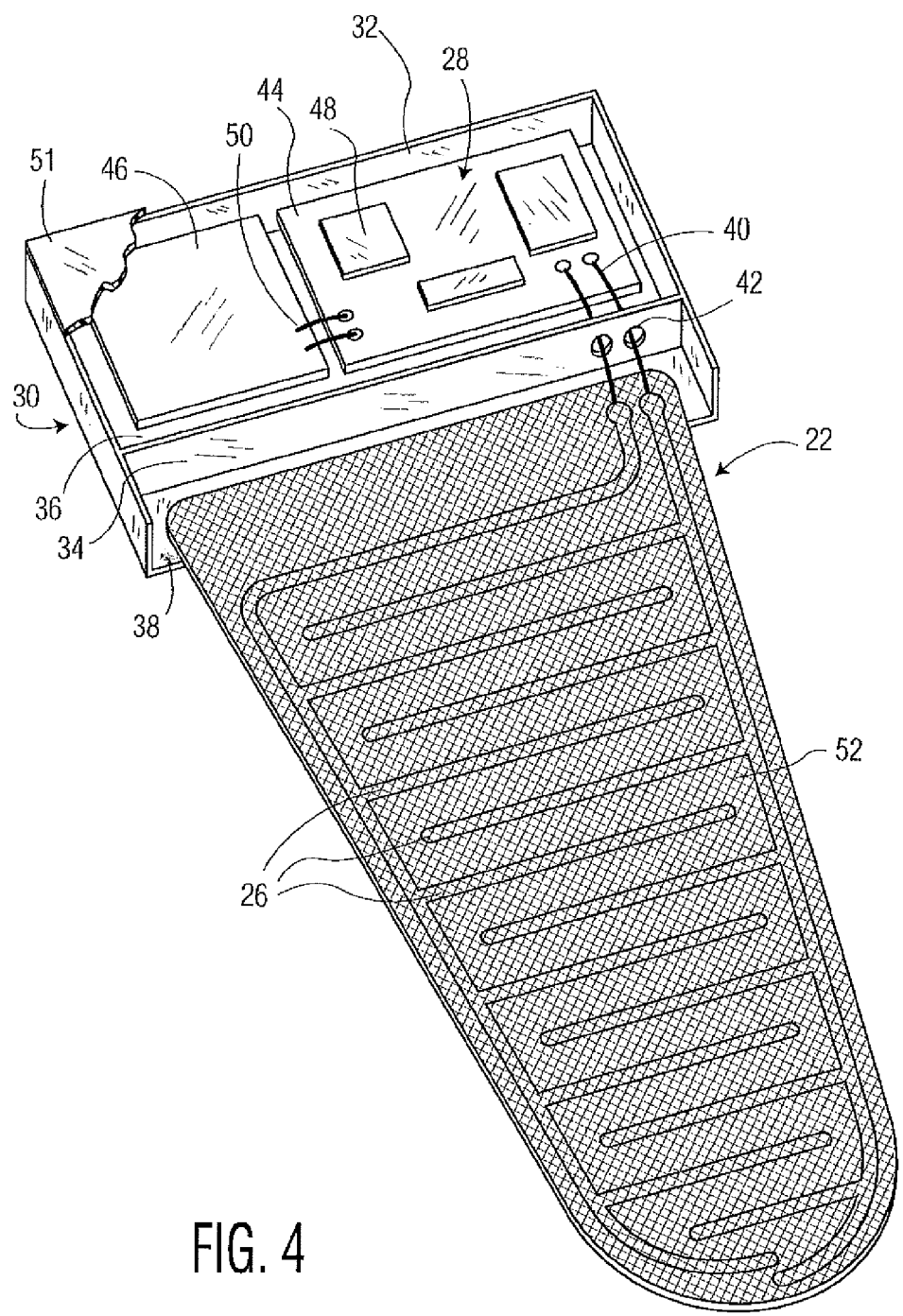
FIG. 4 is a front, left side, bottom isometric view of the apparatus of the present invention prior to connection of the sensor and porous sheet to the case, as shown in FIG. 2, and with the cover removed from the case.

With further reference to FIGS. 1 and 4, it is illustrated therein that a porous sheet 52 is positioned over or on top of sensor 22. Again, porous sheet 52 is intended to contact the skin of the user of apparatus 10 and to prevent a false signal being generating by moisture sensor 22 through natural body moisture of a patient. Porous sheet 52 is shown in the form of a mesh fabric sheet that is illustrated in FIGS. 1 and 4 as allowing the viewing of first surface 14 and metal traces 26 of sensor 22, thereupon. Specifically, porous sheet 52 may take the form of a polyester mesh, product number WS0800 distributed by Industrial Netting Corporation of Minneapolis, Minn. Mesh sheet 52 may possess a thickness of about 0.35 mm., having hole sizes that are approximately 0.8 cm. and possessing an open area of about 58%. Of course, other suitable porous sheets may be employed with apparatus 10 of the present invention. Most importantly, porous sheet 52 is semi-flexible and possesses a memory, the significance of which follows hereinafter. FIG. 2 indicates that porous sheet 52 and moisture sensor 22 lie above shelf 38 of case 30. End 54 of moisture sensor 22 and a portion of porous sheet 52 are held to shelf 38 by an adhesive 56 which may be a potting compound, FIG. 2. Consequently, porous sheet 52 may be separated, rotated, or lifted relative to base member 12 according to directional arrows 58 and 60. Since porous sheet 52 possesses a memory, movement of porous sheet 52 into the position depicted in FIG. 2 allows porous sheet 52 to be cleaned and dried. Upon release of porous sheet 52 by a user, porous sheet 52 will return itself to a position over moisture sensor 22, as indicated by directional arrow 58.

Apparatus 10 also includes as one of its elements a tilt sensor 48 which lies within case 30. Tilt sensor may take the form of a 3-axis orientation/motion detection sensor, model number MMA7660FC manufactured by Freescale Semiconductor, Inc. of Austin Tex. Tilt sensor 48 tracks a patient's turning motion relative to the head to foot axis of the patient. Upon such motion, a radio signal is generated in a conventional manner by the activation of tilt sensor 48 and, eventually, notifies a care provider when a positional change has taken place in the patient wearing apparatus 10. More specifically, the signal generated by tilt sensor 48 may be programmed to inform a caregiver when a patient wearing device 10 has had insufficient turning movement during a selected time period. Should this occur, the care provider would visit a particular patient and turn the patient in order to avoid the possibility of the patient developing decubitus ulcers. For example, a signal may be generated by tilt sensor 48 when a turning motion of at least 30 degrees in the head to foot axis of the patient has not occurred during selected time periods such as 30 minutes, 60 minutes, 90 minutes, or 120 minutes as the case may be.

Figure 5:
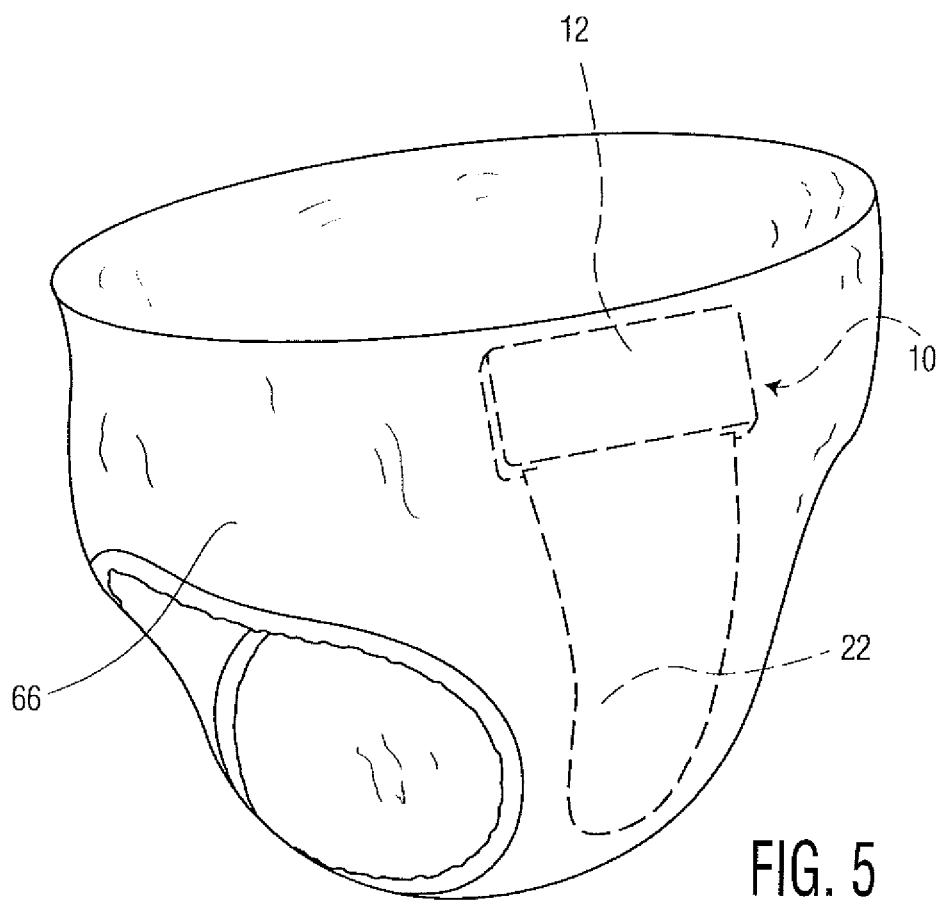
FIG. 5 is a perspective view of an undergarment showing the apparatus of the present invention in place therewithin in dashed line format.
Figure 6:
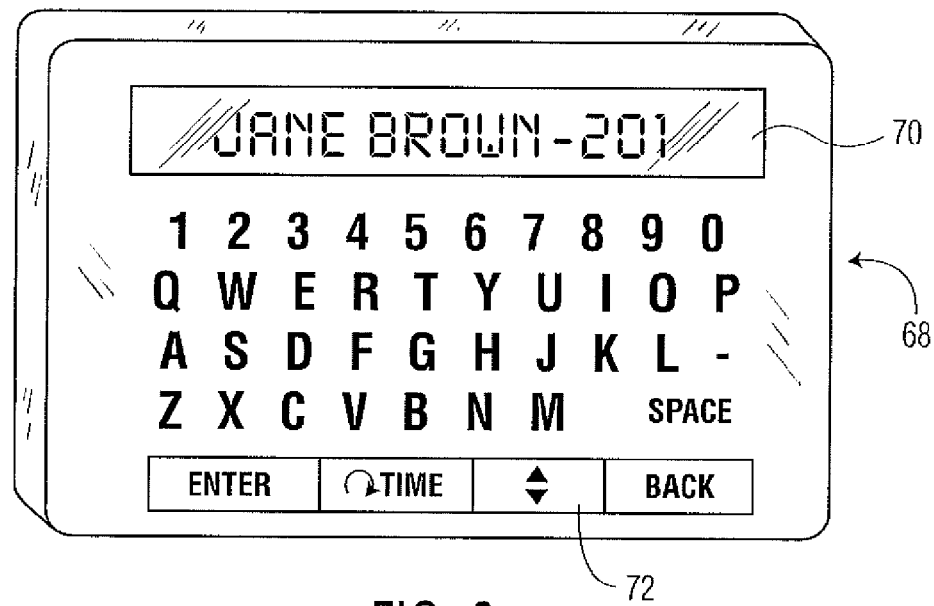
FIG. 6 is a front, top, left side perspective view of a programming unit which is used with the apparatus of the present application depicted in FIGS. 1-4.

In operation, FIG. 5, device 10 has been placed in an undergarment 66 such that second surface 16 of base member 12 lies against the fabric of undergarment 66, while first surface 14, overlain by porous sheet 52, presses against the body of the patient within undergarment 66. In this manner, device 10 is able to detect flow of urine of the patient wearing undergarment 66 via moisture sensor 22 as well as to detect inadequate turning or movement of the patient during selected time periods via the signals generated by tilt sensor 48. By using the programming unit 68, FIG. 6, having a display 70 and a keypad 72, the caregiver may enter the name, room, and bed number, as well as the desired time interval during which a patient must turn at least 30 degrees in the head-foot axis. The wearable moisture position sensor apparatus 10 has a radio receiver and the programming unit 68 has a short range radio transmitter. Previous data is automatically removed and new data entered when keypad 72 is used with programming unit 68 next to the apparatus 10.

Figure 7:
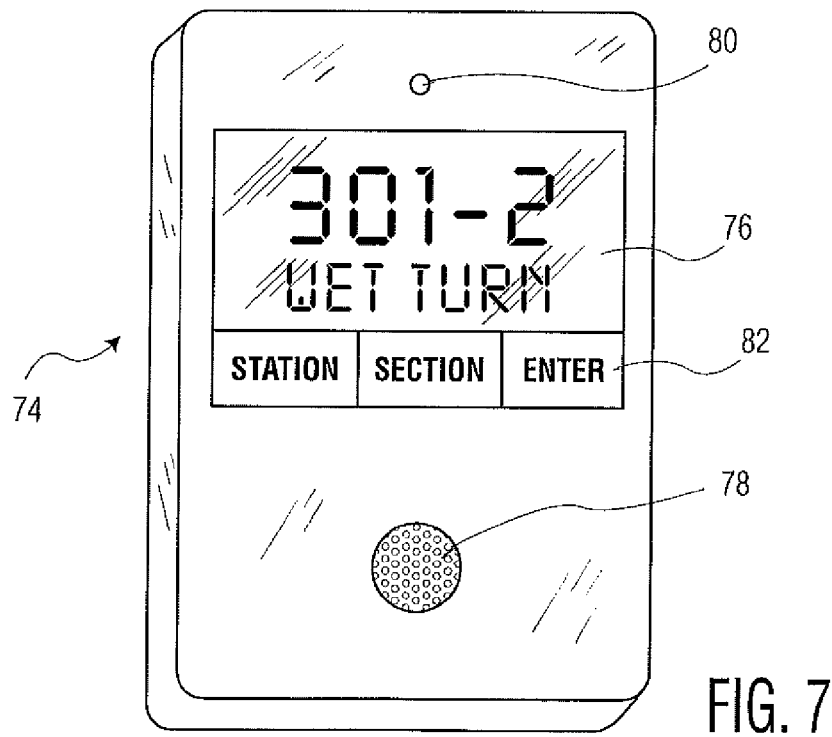
FIG. 7 is a front, left side, bottom perspective view of a handheld monitor which may be employed by a caretaker in conjunction with the apparatus of the present application depicted in FIGS. 1-4.

Monitor 74, FIG. 7, held by the caregiver is capable through display 76 of revealing the name, room, and bed number of patients needing attention. For example, patient locations may be displayed in rotation, one at a time, and remain on display 60 for a period of 5 seconds along with the terms "wet" and/or "turn" being displayed. Once a situation has been corrected by the caregiver, the display will remove this information. In addition, a beeper 78 will initiate an audio alert prior to displaying the information on display 76. Such audio alert will be repeated if the condition causing the alert is not corrected after a certain time, say five minutes. LED 80 indicates a low battery condition as well as a charging status for monitor 74. Keypad 82 may be used to limit items appearing on display 76. Namely, such items may be restricted to a selected nursing station or to a subsection of such station, as the case may be.

While in the forgoing embodiments of the present invention have been set forth in considerable detail for the purposes of making a complete disclosure of the invention, it may be apparent to those skilled in the art that numerous changes may be made in such details without departing from the spirit and principles of the invention.

What is claimed is:

1. A monitor apparatus for positioning within an undergarment adjacent a skin of a patient comprising:
    a base member, said base member including a first surface and an opposite second surfaces, said second surface lying against the undergarment, and said first surface intended to lie against the skin of the patient;
    a moisture sensor, said moisture sensor being mounted to said base member, said moisture sensor configured to generate a signal upon detection of moisture;
    a porous sheet, said porous sheet being mounted to said base member and being able to contact the skin of the patient to prevent a false signal being generated by said moisture sensor;
    a holder for fixing a portion of said porous sheet to said base member to allow rotation of a part of said porous sheet relative to said base member; and
    a tilt sensor, said tilt sensor being mounted to said base, said tilt sensor being configured to generate a signal indicating absence of turning of the patient during a selected time interval.

2. The apparatus of claim 1 in which said porous sheet comprises a mesh fabric.

3. The apparatus of claim 1 in which said moisture sensor comprises a plurality of metallic strips separated from one another, said plurality of metallic strips being mounted to said base.

4. The apparatus of claim 1 in wherein said base member comprises a first and a second compartment.

5. The apparatus of claim 4 in which said first compartment contains a battery, electronics, and said tilt sensor.

6. The apparatus of claim 4 in which a second compartment includes a holder for fixing a portion of said moisture sensor and said porous sheet.

7. The apparatus of claim 6 in which said holder comprises an adhesive potting compound.

8. The apparatus of claim 1 in which wherein a portion of said porous sheet is configured to be separable from said moisture sensor.

9. A patient monitor apparatus for positioning within an undergarment adjacent a skin of the patient, comprising:
    a base member, said base member including a first surface and an opposite second surface, said second surface lying next to the undergarment, and said first surface intended to lie against the skin of the patient;
    a moisture sensor, said moisture sensor being mounted to said base member, said moisture sensor configured to generate a signal upon detection of moisture;
    a porous sheet, said porous sheet being mounted to said base member and being able to contact the skin of the patient to prevent a false signal being generated by the moisture sensor, said porous sheet possessing a memory;
    a holder for fixing a portion of said porous sheet to said base member to allow rotation of a part of said porous sheet relative to said base member; and
    a tilt sensor, said tilt sensor being mounted to said base, said tilt sensor being configured to generate a signal indicating absence of turning of the patient during a selected time interval.

10. The apparatus of claim 9 in which said holder comprises an adhesive.

11. The apparatus of claim 9 in which said porous sheet comprises a mesh.

12. The apparatus of claim 9 in which said base member comprises a first and a second compartment and a portion of said moisture sensor and a portion of said porous sheet are fixed to said second compartments.

13. A patient monitor apparatus for positioning within an undergarment adjacent a skin of the patient, comprising:
    a base member, said base member including a first surface and an opposite second surface, said second surface lying against the undergarment, and said first surface intended to lie against the skin of the patient;
    a moisture sensor, said moisture sensor being mounted to said base member, said moisture sensor configured to generate a signal upon detection of moisture;
    a porous sheet, said porous sheet being mounted to said base member and being able to contact the skin of the patient to prevent a false signal being generated by the moisture sensor;
    a holder for fixing a portion of said porous sheet to said base member to allow rotation of a part of said porous sheet relative to said base member; and
    a tilt sensor, said tilt sensor being mounted to said base, said tilt sensor being configured to generate a signal indicating absence of turning of the patient during a selected time interval.

14. The apparatus of claim 13 in which moisture sensor comprises a plurality of metallic strips separated from one another, said plurality of metallic strips being mounted to said base.

15. The apparatus of claim 13 in which said tilt sensor comprises a multi-axis tilt sensor.

\* \* \* \* \*